United States Patent
Arnett

Patent Number: 5,876,447
Date of Patent: Mar. 2, 1999

[54] SILICONE IMPLANT FOR FACIAL PLASTIC SURGERY

[75] Inventor: G. William Arnett, Santa Barbara, Calif.

[73] Assignee: Implantech Associates, Ventura, Calif.

[21] Appl. No.: 798,749

[22] Filed: Feb. 13, 1997

Related U.S. Application Data

[60] Provisional application No. 60/011,796 Feb. 14, 1996.

[51] Int. Cl.⁶ .................................................. A61F 2/02
[52] U.S. Cl. ................................................... 623/11
[58] Field of Search ..................... 606/69–71; 623/11, 623/10

[56] References Cited

U.S. PATENT DOCUMENTS

| | | |
|---|---|---|
| 3,849,805 | 11/1974 | Leake et al. . |
| 4,344,191 | 8/1982 | Wagner . |
| 4,502,161 | 3/1985 | Wall . |
| 4,531,244 | 7/1985 | Hamas . |
| 4,608,051 | 8/1986 | Reck et al. ................................. 623/10 |
| 4,753,657 | 6/1988 | Lee et al. . |
| 4,778,469 | 10/1988 | Lin et al. . |
| 4,790,849 | 12/1988 | Terino . |
| 4,888,018 | 12/1989 | Giampapa . |
| 4,955,909 | 9/1990 | Ersek et al. . |
| 4,969,901 | 11/1990 | Binder . |
| 5,207,709 | 5/1993 | Picha . |
| 5,236,453 | 8/1993 | Picha . |
| 5,348,788 | 9/1994 | White . |
| 5,545,226 | 8/1996 | Wingo et al. ............................. 623/16 |

FOREIGN PATENT DOCUMENTS

| | | |
|---|---|---|
| 0 370 292 A | 5/1990 | European Pat. Off. .................. 623/11 |
| 2 367 479 | 5/1978 | France ....................................... 606/69 |
| 2040688 | 9/1980 | United Kingdom . |
| WO94/01064 | 1/1994 | WIPO . |

*Primary Examiner*—David H. Willse
*Attorney, Agent, or Firm*—Chadbourne & Parke LLP

[57] ABSTRACT

The facial implant is made of silicone and has a grid of horizontal and vertical grooves on a concave bone-facing rear surface. The grid pattern of grooves imparts flexibility to the implant to facilitate implantation. In addition, the grooves provide for ingrowth of tissue as well as providing reference marks to facilitate implantation of a pair of mirror-image facial implants in a symmetrical manner. The groove depth may be in a range of from 0.5 to 1 millimeter and may also be of variable depth relative to the cross-sectional thickness of the body.

18 Claims, 1 Drawing Sheet

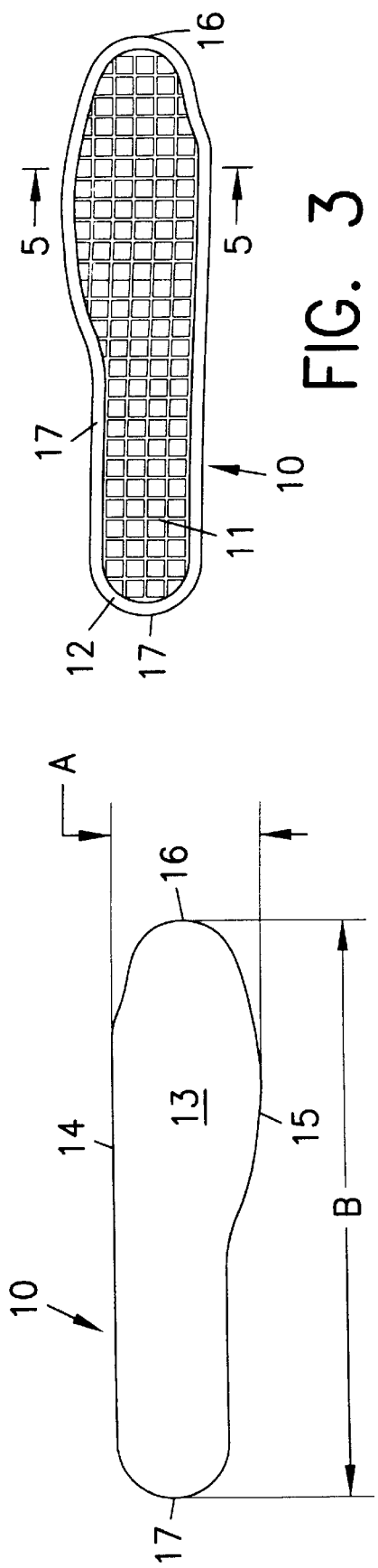
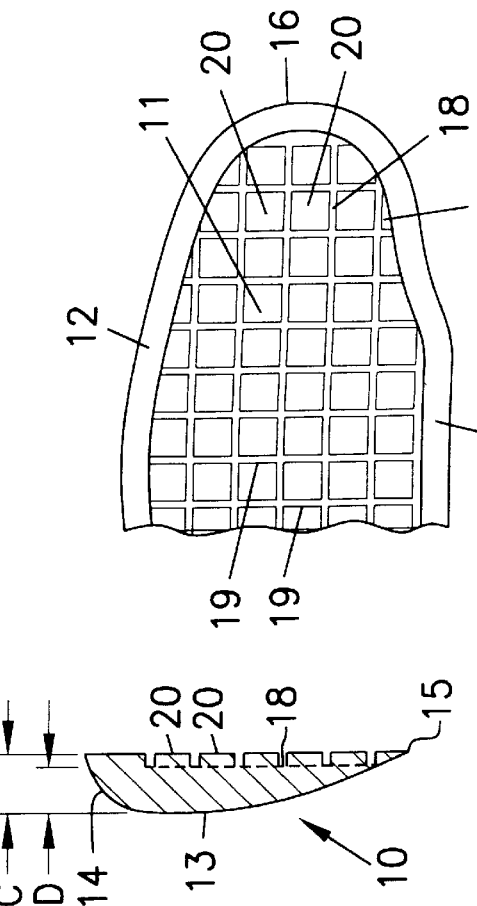
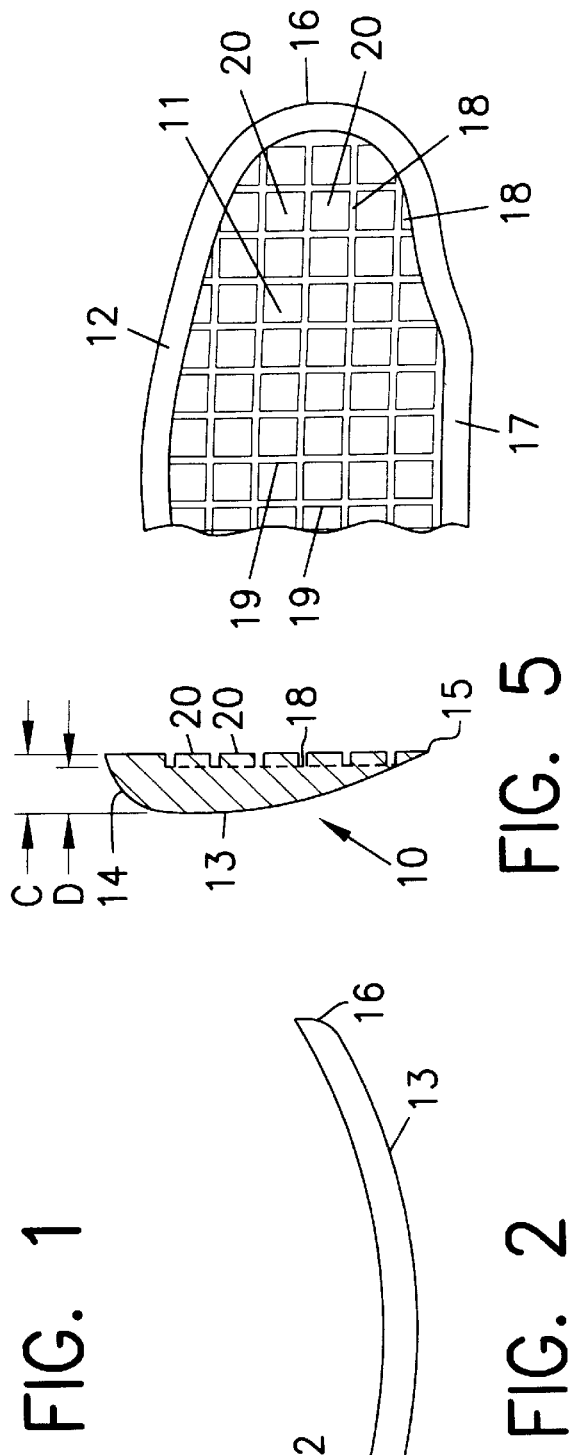

SILICONE IMPLANT FOR FACIAL PLASTIC SURGERY

This application claims the benefit of U.S. Provisional Application No. 60/011,796, filed Feb. 14, 1996.

This invention relates to a silicone implant for facial plastic surgery.

Heretofore, various types of implants have been known for use in plastic surgery and particularly for reconstructive and cosmetic surgery in the facial region. For example, U.S. Pat. No. 4,969,901 describes an implant for use in the submalar region of a person's face. This implant is described as being a relatively thin body with a teardrop-shaped profile. In one form, the posterior and anterior faces of the implant are to be slightly convex and the implant anatomically curved around an arc to facilitate correct fitting of the implant against the supporting facial bones of the patient upon implantation. As further described, the implant is to be secured by a suture which passes through holes in the body of the implant and the overlying tissue.

U.S. Pat. No. 4,790,849 describes another type of malar implant which is comprised of a three dimensional asymmetrical implant which is molded or fashioned from an inert plastic material. The implant generally has an outer surface with a distinct convex surface as well as an inner surface which includes a concave depression to fit the overall contour and curves of the bone of the patient. As described, a pocket is formed in the tissue of the patient in order to receive the implant.

As is apparent, implants of the above type can be difficult to position in an exact manner due to the shapes of the implants and the techniques used for implantation.

Other types of implants have also been known which utilize various techniques for implantation. For example, U.S. Pat. No. 4,753,657 describes a technique for implanting a femoral component of a total replacement hip joint in the femur. As described, use is made of wedges to secure the stem of the implant in a femur. In each case, the wedges are provided with an outer shell of metal having an outer surface with a structured texture so that bone can grow into intimate contact with the surface. In addition, the metal shell may be provided with a series of slots so that the shell is able to deform more easily to conform to the shape of the femoral component as well as the medullary canal of a femur.

Other types of porous structures or structured surfaces for tissue ingrowth to aid in holding an implant in place are described in U.S. Pat. Nos. 5,348,788; 5,207,709; 4,778,469; and 3,849,805.

Submalar-facial implants have also been known from WO94/01064 in which the implant is provided with front and rear surface articulations, i.e. grooves, to provide flexibility to the structure. The articulations are also to act to reduce pressure transmitted to the skin above the implant by absorbing tension therefrom so as to decrease the likelihood of implant erosion or extrusion.

Heretofore, various problems have arisen in attempting to place implants in the malar region of the face particularly where pairs of implants are to be used in a symmetrical manner to achieve desired reconstructive and/or cosmetic results. Because of the generally smooth tear-drop shape of the implants, movement of the implants may occur from time-to-time. Further, matching implantation of one implant relative to another implant of a pair of implants which are to be placed symmetrically can be difficult.

Accordingly, it is an object of the invention to obtain good bone conformation of an implant and a close fit against the somewhat variable contours of facial bones.

It is another object of the invention to prevent slippage between an implant and underlying bone.

It is another object of the invention to accurately place an implant in a facial region of a patient.

It is another object of the invention to obtain accurate symmetrical bilateral positioning of implants.

Briefly, the invention provides a facial implant comprised of a one-piece body having a concave bone-facing rear surface and a convex front surface. In accordance with the invention, the implant has a grid pattern of grooves in the rear surface to impart flexibility to the body.

This grid pattern is sufficient to enable to good conformation and a close fit against the somewhat variable contours of facial bones. The grid pattern also provides a "non-skid" surface for increased friction between the implant and underlying bone which stabilizes and permits accurate placement of the implant during surgical installation.

The grid pattern of grooves also provides for the ingrowth of tissue. That is to say, the underlying tissue will grow into the grooves of the grid pattern during a healing phase to hold the implant more securely in place.

The invention further provides a pair of mirror-image facial implants each of which is comprised of a one-piece body as above with a grid pattern of grooves on the rear surface to impart flexibility. In addition, the horizontal grooves in each implant provide reference marks for bilateral positioning of the pair of implants in symmetrical relation. Such a pair of mirror-image implants are particularly suitable in bilateral cosmetic surgery where the implants are installed on opposite sides of a face.

These and other objects and advantages of the invention will become more apparent from the following detailed description taken in conjunction with the accompanying drawings wherein:

FIG. 1 illustrates a front view of an implant constructed in accordance with the invention;

FIG. 2 illustrates a plan view of the implant of FIG. 1;

FIG. 3 illustrates a rear view of the implant of FIG. 1 as constructed in accordance with the invention;

FIG. 4 illustrates an enlarged view of a section of the rear of the implant of FIG. 1; and FIG. 5 illustrates a view taken on line 5—5 of FIG. 3.

Referring to FIG. 1, the facial implant 10 is made of silicone and is of a style useful in augmenting facial contours in the malar region of the face. The general shape of the implant will vary depending on the specific area of implantation.

As illustrated in FIG. 2, the implant 10 has a concave bone-facing rear surface 12 and a convex front surface 13. As shown in FIG. 1, the shape of the body 10 is variable with a linear top edge 14, a curvilinear bottom edge 15, a first rounded end portion 16 and an opposite rounded end portion 17.

As shown in FIGS. 3 and 5, the implant 10 enlarges in a region adjacent the end portion 16 but this feature is specific to the illustrated implant and is not an essential feature of the implant. As indicated in FIG. 5, the implant is of a maximum thickness adjacent the top edge 14 and tapers to a thin feather edge at the bottom edge 15. Again, this feature is specific to the illustrated implant and not an essential feature.

Referring to FIGS. 3 and 4, a grid pattern 11 of crossing grooves 18, 19 is formed in substantially the entire bone-facing rear surface 12 of the implant 10 with the exception of a border 17 forming the perimeter of the rear surface 12. The grid pattern 11 is formed by horizontal grooves 18 and vertical grooves 19. The grooves 18, 19 are molded into the implant 10 to provide a checkerboard-like pattern of square surfaces 20 between the grooves 18, 19. The horizontal and vertical grooves 18, 19 are respectively spaced apart about 2 to 3 millimeters and are about 0.5 to 1 millimeter in width. However, these dimensions may vary somewhat depending on the specific style of the implant. Other typical implant dimensions are as follows:

| SIZE | A(mm) | B(mm) | C(mm) |
|------|-------|-------|-------|
| –03  | 17    | 63    | 3.0   |
| –04  | 17    | 63    | 4.0   |
| –05  | 17    | 63    | 5.0   |
| –06  | 18    | 65    | 6.0   |
| –07  | 18    | 65    | 7.0   |

Referring to FIG. 5, the depth of the grooves 18, 19 is constant and in the range of 0.5 to 1 millimeter. In the presently preferred embodiment, however, the groove depth is proportional to the implant cross-sectional thickness with greater groove depth in areas of greater implant thickness. In FIG. 5, the dimension "C" represents the overall implant cross-sectional thickness and the dimension "D" represents the thickness measured from the front surface 13 to the base of a groove. In the preferred embodiment, the groove depth is varied to maintain the relation C minus D at a value of about 2 to 3 millimeters, thus providing the implant with enhanced flexibility.

A key feature of the implant is that the grid pattern 11 imparts flexibility to the implant enabling good bone conformation and a close fit against the somewhat variable contours of facial bones. The grid pattern 11 also provides a "non-skid" surface for increased friction between implant and underlying bone which stabilizes and permits accurate placement of the implant during surgical installation. Underlying tissue will grow into the depressed grooves of the grid pattern 11 during the healing phase to hold the implant 10 more securely in place.

In bilateral cosmetic surgery where two mirror-image implants are installed on opposite sides of a face, the grid pattern 11 provides reference marks which assist the surgeon in obtaining symmetrical bilateral positioning. Typically, the implant is sold in pairs only.

If implant trimming is needed, the grid pattern 11 also assists the surgeon in achieving accurate symmetrical recontouring of the right and left implants.

The invention thus provides a facial implant which has enhanced flexibility to facilitate implantation, particularly in a malar region of a face.

The invention further provides an implant with a grid pattern of grooves which not only provides for tissue ingrowth to secure the implant in place but also provides reference marks to facilitate placement of a pair of mirror image implants in a symmetrical manner.

What is claimed is:

1. A facial implant for reconstructive and cosmetic surgery comprising
   a one piece body molded into a desired shape to augment facial contours, said body having a concave bone facing rear surface and a convex front surface; and
   a grid pattern in said rear surface having horizontal and vertical grooves defining a pattern of square surfaces and imparting flexibility to said body.

2. A facial implant as set forth in claim 1 wherein each said groove is of a constant depth in a range of from 0.5 to 1 millimeter.

3. A facial implant as set forth in claim 1 wherein each groove has a depth of from 2 to 3 millimeters.

4. A facial implant as set forth in claim 1 wherein said body has a variable cross-sectional thickness and at least some of said grooves have a depth proportional to said cross-sectional thickness of said body.

5. A facial implant as set forth in claim 4 wherein each of said grooves has a variable depth of between 2 and 3 millimeters.

6. A facial implant as set forth in claim 1 wherein said grooves are spaced apart a distance of 2 to 3 millimeters and have a width of 0.5 to 1 millimeters.

7. A facial implant as set forth in claim 1 wherein said body is of greater height at one end than the opposite end thereof.

8. A facial implant as set forth in claim 7 said body tapers to a thin feather edge at said opposite end.

9. A facial implant for reconstructive and cosmetic surgery comprising
   a one piece body of silicone molded into a desired shape to augment facial contours, said body having a concave bone-facing rear surface and a convex front surface; and
   a grid pattern of crossing grooves in said rear surface for ingrowth of tissue, said grooves imparting flexibility to said body.

10. An implant as set forth in claim 9 wherein each said groove is of a constant depth in a range of from 0.5 to 1 millimeter.

11. An implant as set forth in claim 9 wherein said body has a variable cross-sectional thickness and at least some of said grooves have a depth proportional to said cross-sectional thickness of said body.

12. An implant as set forth in claim 11 wherein each of said grooves has a variable depth of between 2 and 3 millimeters.

13. An implant as set forth in claim 9 wherein said grooves are spaced apart a distance of 2 to 3 millimeters and have a width of 0.5 to 1 millimeters.

14. A pair of mirror-image facial implants for reconstructive and cosmetic surgery, each implant comprising
   a one-piece body molded into a desired shape to augment facial contours, said body having a concave bone-facing rear surface and a convex front surface; and
   a grid pattern of grooves in said rear surface to impart flexibility to said body having horizontal and vertical grooves defining a pattern of square surfaces, wherein said horizontal and vertical grooves provide reference marks for bilateral positioning of said pair of implants in symmetrical relation.

15. A pair of implants as set forth in claim 14 wherein each said groove is of a constant depth in a range of from 0.5 to 1 millimeter.

16. A pair of implants as set forth in claim 14 wherein said body has a variable cross-sectional thickness and at least some of said grooves have a depth proportional to said cross-sectional thickness of said body.

17. A pair of implants as set forth in claim 16 wherein each of said grooves has a variable depth of between 2 and 3 millimeters.

18. A pair of implants as set forth in claim 14 wherein said grooves are spaced apart a distance of 2 to 3 millimeters and have a width of 0.5 to 1 millimeters.

* * * * *